United States Patent [19]
Romeo et al.

[11] Patent Number: 5,849,717
[45] Date of Patent: Dec. 15, 1998

[54] O-SULFATED GANGLIOSIDES AND LYSO-GANGLIOSIDE DERIVATIVES

[75] Inventors: Aurelio Romeo, Rome; Gunter Kirschner, Abano Terme; Carlo Chizzolini, Padova, all of Italy; Hari Manev, Pittsburgh, Pa.; Laura Facci, Vicenza, Italy

[73] Assignee: Fidia S.p.A., Abano Terme, Italy

[21] Appl. No.: 530,275

[22] PCT Filed: Mar. 4, 1994

[86] PCT No.: PCT/US94/01965

§ 371 Date: Jan. 31, 1996

§ 102(e) Date: Jan. 31, 1996

[87] PCT Pub. No.: WO94/20515

PCT Pub. Date: Sep. 15, 1994

[30] Foreign Application Priority Data

Mar. 4, 1993 [IT] Italy ................. PD93A0045

[51] Int. Cl.[6] ............... A61K 31/70; C07H 15/00
[52] U.S. Cl. ............. 514/25; 536/17.2; 536/17.5; 536/17.6; 536/17.9
[58] Field of Search .............. 514/25; 536/17.2, 536/17.5, 17.6, 17.9

[56] References Cited

U.S. PATENT DOCUMENTS 5,264,424  11/1993  Della Valle et al. ............ 514/54

FOREIGN PATENT DOCUMENTS 0433112  6/1991  European Pat. Off. .
03-246297  11/1991  Japan .
WO93/03049  2/1993  WIPO .

OTHER PUBLICATIONS

Greene *Scientific American* Sep. 1993, 269(3), 99–105.
Fauci *Proc. Natl. Sci. USA* Dec. 1986, 83(24), 9278–9283.
Olney *Annu. Rev. Pharmacol. Toxicol.* 1990, 30, 47–71.
Tiemeyer, et al., "Ganglioside–specific . . .", *The Journal of Biological Chemistry*, vol. 264, No. 3, Jan. 25, 1989, pp. 1671–1681.
Achinami, et al., Prep. of gangliosides . . . ,*Chem. Abst.*, No. 8362Z, vol. 117, No. 1, Jul. 6, 1992, pp. 847–848.
Handa et al., "Inhibition of Infection . . . ", *Biochemical and Biophysical* . . ., vol. 175, No. 1, Feb. 28, 1991, pp. 1–9.

*Primary Examiner*—Kathleen K. Fonda
*Attorney, Agent, or Firm*—Birch, Stewart, Kolasch & Birch, LLP

[57] ABSTRACT

Disclosed are derivatives of gangliosides and of N-acyl-N-lyso-gangliosides, of N'-acyl-N'-lyso-gangliosides and N,N'-di- or poly-acyl-N,N'-di-lyso-gangliosides, in which at least one of the hydroxyl groups in the saccharide, sialic or ceramide residues is esterified with sulfuric acid, functional derivatives thereof, and their salts with either inorganic or organic bases and the acid addition salts, except persulfated derivatives at the hydroxyl, sialic and ceramide groups of the $GM_1$, $GD_{1a}$, $GD_{1b}$ and $GT_{1b}$ gangliosides. Such compounds have antineurotoxic and neurotogenic activity and may therefore be used in pharmaceutical preparations. Also a marked modulating effect on the expression of the $CD_4$ molecule in immune system cells has been shown.

30 Claims, No Drawings

O-SULFATED GANGLIOSIDES AND LYSO-GANGLIOSIDE DERIVATIVES

This application is based on PCT International Application Number PCT/US94/01965 filed Mar. 4, 1994.

OBJECT OF THE INVENTION

The present invention relates to novel derivatives of gangliosides and of N-acyl-N-lyso-gangliosides, of N'-acyl-N'-lyso-gangliosides and N,N'-di- or poly-acyl-N,N'-dilyso-gangliosides, whereof at least one of the hydroxyl groups of the saccharide, sialic or ceramide residues is esterified with sulfuric acid, the functional derivatives thereof, and their salts with either inorganic or organic bases and the acid addition salts, except persulfated derivatives at their hydroxyl groups in the saccharide, sialic and ceramide moieties of the gangliosides $GM_1$, $GD_{1a}$, $GD_{1b}$, and $GT_{1b}$.

Furthermore, the present invention concerns pharmaceutical preparations comprising the novel derivatives of gangliosides mentioned above and their therapeutical application.

The novel derivatives have interesting pharmacological properties, especially protective activity against neurotoxicity induced by excitatory amino acids, such as glutamic acid, and are therefore foreseen to be used in therapy for the nervous system, such as for conditions following degeneration or lesions, i.e. ischemia, hypoxia, epilepsy, trauma and compression, metabolic dysfunction, aging, toxic-infective diseases and chronic neurodegeneration, such as Alzheimer's disease, Parkinson's disease or Huntington's chorea.

The novel compounds of the invention, thanks to their neuritogenic activity, may be used advantageously in therapies aimed at nervous function recovery, such as in peripheral neuropathies and pathologies associated with neuronal damage.

Moreover, certain novel derivatives which are object of the present invention have valuable properties for the modulation of the expression of specific determinants, such as $CD_4$, present on the surface of human cells belonging to the immune system.

The ability of the above compounds to modulate expression of the $CD_4$ molecule, a membrane glycoprotein expressed in various cell types such as thymocytes, lymphocytes, monocytes and macrophages, has great applicative potential in a wide range of human pathologies.

The novel derivatives of the present are contemplated to be used therapeutically in all situations wherein it is necessary to prevent and/or treat infections involving $CD_{4+}$ cells, such as in infections, the etiological agents whereof are microorganisms belonging to the human immunodeficiency (HIV) family of viruses.

Moreover, modulation of $CD_4$ is useful in systemic or organ-specific autoimmune diseases, such as multiple sclerosis, rheumatoid arthritis, chronic polyarthritis, lupus erythematosus, juvenile-onset diabetes mellitus, and also to prevent the phenomenon of organ transplant rejection as well as rejection by the transplanted material against the host, as in the case of bone marrow transplant, and in all cases where the desired effect is to obtain tolerance towards "self" and "non-self" antigens.

The term "N,N'-di-lyso-gangliosides" in the aforesaid definition means a ganglioside from which the natural acyl groups have been removed from the neuraminic nitrogen (N') and from the sphingosine nitrogen (N) thus leaving free amino groups; the word "-di" stands thus to indicate the two positions N and N', but not the actual number of the free amino groups which, depending on the number of sialic acids present, can be more than 2. The expression "N-acyl-N'-di-" or "poly-acyl" is used in the case of synthetic analogues of gangliosides substituted in both the positions N and N'.

The functional derivatives of the abovesaid semisynthetic ganglioside analogues are for example the esters and amides of the carboxyl groups of sialic acid residues, and may also be inner esters with lactone bonds between the sialic carboxyl groups and the hydroxyls of the oligosaccharide, analogous to those known in the case of gangliosides, and possibly also the derivatives of all these compounds, the hydroxyl groups thereof being esterified with organic acids.

Of particular interest are the metal salts of the sulfated groups of the novel compounds and possibly also the salts of any free sialic carboxylic groups, such as sodium, potassium, calcium, magnesium, ammonium salts. Other interesting salts are derived from organic bases, especially therapeutically acceptable bases. Also included in the present invention are salts deriving from metals or bases, not normally used in therapy, and such salts may be possibly used for the purification of the novel products. The acid-addition salts can be formed for example in derivatives where the sphingosine or neuraminic amino group is free.

The aforesaid semisynthetic ganglioside analogues are novel.

Another aspect of the present invention relates to the use of these novel compounds in therapy, especially to treat the abovementioned disorders affecting the central or peripheral nervous systems or the immune system. Still another aspect of the invention relates to pharmaceutical preparations containing one or more of the novel compounds, optionally together with a pharmaceutical excipient or vehicle.

Still another aspect of the invention relates to the use of the compounds disclosed, i.e. the poly-sulfated derivatives at their hydroxyl groups in the saccharide, sialic and ceramide parts of the gangliosides $GM_1$, $GD_{1a}$, $GD_{1b}$ and $GT_{1b}$, in the therapy and in pharmaceutical preparations for the therapy of neurotoxic conditions and conditions where their neuritogenic activity can be utilized.

The acyl groups present in position N and N' of the new ganglioside derivatives can be those of the gangliosides themselves, or they can be acyl groups synthetically inserted into N,N'-dilyso-gangliosides or N-lyso-gangliosides or N'-lyso-gangliosides. The N-lyso-ganglioside derivatives are often reported in literature simply as "lyso-gangliosides" and this nomenclature is partially used also in the present description.

The acyl groups acylating the sphingosine (N) and/or the neuraminic (N') positions may derive from aliphatic acids and have preferably a maximum of 24 carbon atoms, especially between 12 and 16 carbon atoms and are straightchained, or from acids having between 1 and 11 carbon atoms and a straight or branched chain, such as formic acid, acetic acid, propionic acid, butyric acids, valeric acids, especially n-valeric acid, isovaleric acid, trimethylacetic acid, caproic acid, isocaproic acid, heptanoic acid, caprylic acid, pelargonic acid, capric acid and undecanoic acid, di-tert-butyl-acetic acid and 2-propyl-valeric acid, as well as lauric, myristic, palmitic, oleic, elaidic, and stearic acid, eicosancarbonic acid and docosanoic acid. The acyl radicals may also derive from aliphatic acids substituted with one or more polar units, such as halogens, in particular chlorine, bromine and fluorine, free or esterified hydroxyl groups, ketone, ketal and acetal groups derived from aliphatic or lower araliphatic alcohols, ketoxy or aldoxy or hydrazone groups, free or esterified mercapto groups with a lower aliphatic or araliphatic acid or etherified with lower aliphatic or araliphatic alcohols, free or esterified carboxyl groups, free or esterified sulfonic groups with lower aliphatic or araliphatic alcohols, sulfamide groups substituted with lower alkyl or aralkyl groups, sulfoxide or sulfone groups derived from lower alkyl or lower alkyl groups, nitril groups, free or substituted amino groups, and ammonium derivatives of such amino groups.

In the present specification, the term "lower" means groups with a maximum of 6 carbon atoms unless otherwise indicated.

Other acyl radicals acylating one or both of the sphingosine and neuraminic amino groups of the new derivatives may also be those of an aromatic, araliphatic, cycloaliphatic, aliphatic-cycloaliphatic or heterocyclic acid.

Aromatic acyl groups are mainly those deriving from benzoic acid or its homologues wherein the phenyl residue is substituted with, for example, 1 to 3 $C_{1-4}$ alkyl or alkoxy groups, especially methyl and methoxy groups, and/or with one of the polar groups mentioned as substituents in the aliphatic acyl radical, for example free or alkylated amino groups.

Araliphatic acyl groups have preferably a $C_{2-4}$ alkylene chain as the aliphatic portion, and the aromatic portion is preferably one of the above defined aromatic groups. Cycloaliphatic acyl radicals are preferably those deriving from an alicyclic hydrocarbon having between 3 to 6 carbon atoms in the ring, such as cyclopropane, cyclobutane, cyclopentane and cyclohexane. Heterocyclic radicals derive preferably from a monocyclic heterocyclic compound with just one heteroatom link, such as —O—, —N=, —NH—, or —S— and may be aromatic or aliphatic by nature, such as acids of the pyridine group, for example nicotinic or isonicotinic acid of the furane group, such as 2-furoic acid, or of the thiophene group, such as 3-thiophene acetic acid, the imidazole group, such as the 4-imidazole-acetic acid, or of the pyrrole group, such as 1-methyl-2-pyrrole-carboxylic acid.

Functional derivatives of the novel semisynthetic ganglioside derivatives according to the present invention are esters, inner esters and amides of the sialic carboxyl groups. The ester groups are particularly derived from aliphatic alcohols and especially from those with a maximum of 12 and preferably 6 carbon atoms, or from araliphatic alcohols with preferably one single benzene ring, optionally substituted with 1–3 $C_{1-4}$ alkyl groups, for example methyl groups, and with a maximum of 4 carbon atoms in the aliphatic chain, or from alicyclic or aliphatic-alicyclic alcohols with one single cycloaliphatic ring and a maximum of 14 carbon atoms, or from heterocyclic alcohols with a maximum of 12 carbon atoms and preferably 6, and one single heterocyclic ring containing a heteroatom link chosen from the group formed by —N=, —NH—, —O—, and —S—.

The amido groups of the carboxyl functions derive from ammonia or from amines of any class, preferably with a maximum of 12 carbon atoms. Special mention should be made of lower aliphatic amines, such as methylamine, ethylamine, propylamine, and butylamine.

Said esterifying alcohols and amidating amines can then be substituted, especially with functions chosen from the groups formed by hydroxyl, amino, alkoxyl groups with a maximum of 4 carbon atoms, carboxyl or carbalkoxyl with a maximum of 4 atoms in the alkyl residue, alkylamino or dialkylamino with a maximum of 4 carbon atoms in the alkyl moieties, and they may be saturated or unsaturated, especially with one double bond. The alcohols may be monovalent or polyvalent, particularly bivalent. Of the aliphatic alcohols, special mention should be made of the lower alcohols with a maximum of 6 carbon atoms, such as methyl alcohol, ethyl alcohol, propyl alcohol and isopropyl alcohol, n-butyl alcohol, isobutyl alcohol, tert-butyl alcohol and, of the bivalent alcohols, ethylene glycol and propylene glycol. Of the araliphatic alcohols, special mention should be made of those with just one benzene residue, such as benzyl alcohol and phenethyl alcohol; of the alicyclic alcohols, preference is given to those with only one cycloaliphatic ring, such as cyclohexyl alcohol (cyclohexanol) or terpene alcohols. Among the heterocyclic alcohols, special mention should be made of tetrafuranol and tetrapyranol.

In the partially sulfated derivatives, i.e. derivatives in which not all of the hydroxyl groups have been sulfated, according to the present invention, the other hydroxyl groups can in turn be esterified with organic aliphatic, aromatic, araliphatic or heterocyclic acids, which acids can be the same as those defined as acylating the above-mentioned N and N' amino groups. The partial sulfuric esters of the present invention represent generally mixtures of different position isomers.

The sulfated compounds are easily converted into their metal or organic base salts, for example into their alkali metal salts, especially sodium salts, by treatment with bases or basic salts, for example, in the case of sodium salts, with sodium carbonate. Especially for therapeutic applications, the sulfate esters are used in the form of such salts, especially sodium salts.

Among the most important basic gangliosides to be used in the preparation of the novel derivatives, mention can be made of for example those wherein the oligosaccharide is formed by a maximum of 4 saccharide units, and wherein the saccharide portion is unitary. It is preferable to choose hexoses from the group formed by N-acetylglucosamine and N-acetylgalactosamine. The gangliosides of said group are for example extracted from vertebrate brains, such as those described in the article "Gangliosides of the Nervous System" in "Glycolipid Methodology", Lloyd A., Witting Fd., American Oil Chemists Society, Champaign, III, 187–214 (1976) (see in particular FIG. 1), for example gangliosides $GM_4$, $GM_3$, $GM_2$, $GM_1$-GlcNAC, $GD_2$, $GD_{1a}$-GalNAC, $GT_{1c}$, $G_Q$, $GT_1$, and particularly those wherein the oligosaccharide contains at least one glucose residue or one galactose residue and one N-acetylglucosamine residue or N-acetylgalactosamine residue and above all the following:

$GM_1$
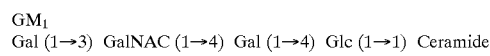
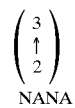
NANA $GD_{1a}$
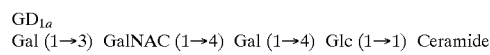
NANA          NANA GD$_{1b}$
Gal (1→3) GalNAC (1→4) Gal (1→4) Glc (1→1) Ceramide

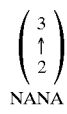
NANA

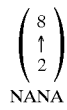
NANA

GT$_{1b}$
Gal (1→3) GalNAC (1→4) Gal (1→4) Glc (1→1) Ceramide

NANA

NANA

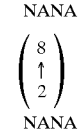
NANA where Glc stands for glucose, GalNAC stands for N-acetylgalactosamine, Gal stands for galactose, NANA stands for N-acetylneuraminic acid.

One group of new derivatives according to the invention is represented by the following formula (I), wherein it is clear that not all the R symbols can be at the same time H and with the exclusion of the persulfated (totally sulfated) derivatives of GM$_1$, GD$_{1a}$, GD$_{1b}$, GT$_{1b}$ gangliosides already mentioned.

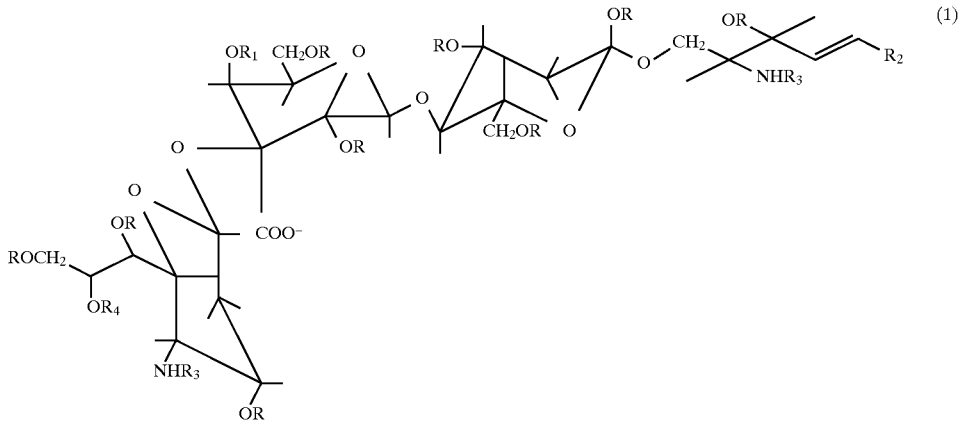

wherein R=H or SO$_3$H, with the exclusion of the case where all the R=H.

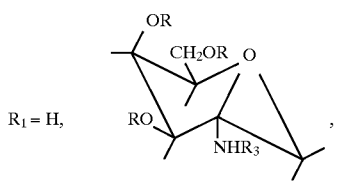

R$_1$ = H,

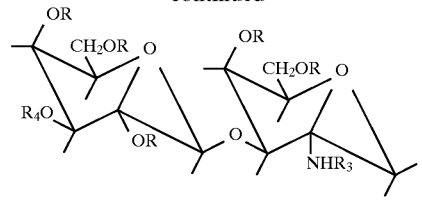

R$_2$=—(CH$_2$)$_n$—CH$_3$, n=12–14
R$_3$=H or acyl

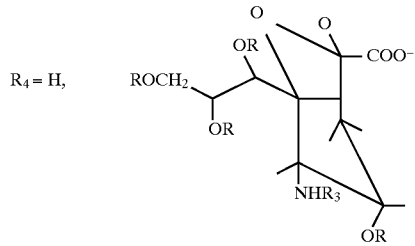

R$_4$ = H, the persulfated derivatives of GM$_1$, GD$_{1a}$, GD$_{1b}$, GT$_{1b}$ gangliosides being excluded.

The excluded derivatives are actually described in the paper Biochemical and Biophysical Research Communications Vol. 175, No. 1, Feb. 28th, 1991.

Of the specific compounds of particular interest, special mention should be made of the monosulfated derivatives of the following ganglioside derivatives:

N-acetyl-lyso-GM$_1$
N-dichloroacetyl-lyso-GM$_1$
N-phenylacetyl-lyso-GM$_1$
N-propionyl-lyso-GM$_1$
N-trimethylacetyl-lyso-GM$_1$
N-trimethoxybenzoyl-lyso-GM$_1$
N-nicotinoyl-lyso-GM$_1$
N-capronyl-lyso-GM$_1$
N-octanoyl-lyso-GM$_1$
N-decanoyl-lyso-GM$_1$
N-undecanoyl-lyso-GM$_1$
N-4-chlorobenzoyl-lyso-GM$_1$
N-4-benzoyl-lyso-GM$_1$
N-2-bromoacetyl-lyso-GM$_1$ in the form of mixture of sulfated isomers in different positions, and the corresponding poly-sulfated derivatives.

Of particular interest are the mono- or poly-sulfated derivatives corresponding to the aforesaid compounds, but acylated in position N', i.e. the mono- or polysulfated derivatives of N'-acetyl-N,N'-dilyso-$GM_1$
N'-dichloroacetyl-N,N'-dilyso-$GM_1$
N'-phenylacetyl-N,N'-dilyso-$GM_1$
N'-propionyl-N,N'-dilyso-$GM_1$
N'-trimethylacetyl-N,N'-dilyso-$GM_1$
N'-trimethoxybenzoyl-N,N'-dilyso-$GM_1$
N'-nicotinoyl-N,N'-dilyso-$GM_1$
N'-capronyl-N,N'-dilyso-$GM_1$
N'-octanoyl-N,N'-dilyso-$GM_1$
N'-decanoyl-N,N'-dilyso-$GM_1$
N'-undecanoyl-N,N'-dilyso-$GM_1$
N'-4-chlorobenzoyl-N,N'-dilyso-$GM_1$
N'-4-benzoyl-N,N'-dilyso-$GM_1$
N'-2-bromoacetyl-N,N'-dilyso-$GM_1$ in the form of mixture of sulfated isomers in different positions.

Another interesting group of compounds is the mono- or polysulfated derivatives of N,N'-diacyl-N,N'-dilyso-gangliosides deriving from $GM_1$, such as N,N'-diacetyl-N,N'-dilyso-$GM_1$
N,N'-di(dichloroacetyl)-N,N'-dilyso-$GM_1$
N,N'-di(phenylacetyl)-N,N'-dilyso-$GM_1$
N,N'-di(propionyl)-N,N'-dilyso-$GM_1$
N,N'-di(trimethylacetyl)-N,N'-dilyso-$GM_1$
N,N'-di(trimethoxybenzoyl)-N,N'-dilyso-$GM_1$
N,N'-di(nicotinoyl)-N,N'-dilyso-$GM_1$
N,N'-di(capronyl)-N,N'-dilyso-$GM_1$
N,N'-di(octanoyl)-N,N'-dilyso-$GM_1$
N,N'-di(decanoyl)-N,N'-dilyso-$GM_1$
N,N'-di(undecanoyl)-N,N'-dilyso-$GM_1$
N,N'-di(4-chlorobenzoyl)-N,N'-dilyso-$GM_1$
N,N'-di(4-benzoyl)-N,N'-dilyso-$GM_1$
N,N'-di(2-bromoacetyl)-N,N'-dilyso-$GM_1$ in the form of mixtures of sulfated isomers in different positions.

As concerns gangliosides, special mention should be made of the mono- and poly-sulfated ganglioside derivatives as emphasized above, and thus mono- and poly-sulfated derivatives of gangliosides $GM_1$, $GD_{1a}$, $GD_{1b}$, $GT_{1b}$, $GM_2$, $GM_3$, $GM_4$, $GM_1$-glcNAC, $GD_2$, $GD_{1a}$-GalNAC, $GT_{1c}$, $G_Q$, $GT_1$.

All these compounds can be easily converted into their metal salts, especially sodium salts, and these have particular importance in consideration of their possible therapeutical applications.

It is well known that gangliosides are glycosphingolipids containing sialic acid with a basic saccharide structure bound to ceramide and one or more molecules of sialic acid. The saccharide portion presents at least a galactose or glucose and one N-acetylglucosamine or N-acetylgalactosamine.

The general structure of a ganglioside can so be represented as follows:

One mole of sialic acid $\begin{cases} \text{- One mole of ceramide} \\ \text{- At least one mole of galactose} \\ \quad \text{or glucose} \\ \text{- At least one mole of N-acetylglu-} \\ \quad \text{cosamine or N-acetylgalactosamine} \end{cases}$ where all the components are bound by glucosidic bonds.

A large number of gangliosides have been identified which are particularly abundant in the nervous tissue, especially in the cerebral one (Ando S.: Gangliosides in the nervous system. Neurochem. Int. 5, 507537, 1983).

It has been widely demonstrated that gangliosides are able to enhance functional recovery both in the lesioned Peripheral Nervous System (PNS) and Central Nervous System (CNS), through the involvement of specific membrane mechanisms and the interaction with trophic factors, as pointed out from studies in vitro on neuronal cultures (Ferrari F. et al.: Dev. Brain Res., 8:215–221, 1983; Doherty P. et al., J. Neurochem. 44: 1259–1265, 1985; Skaper S. D. et al., Mol. Neurobiol. 3: 173–199, 1989).

Moreover, it has been shown that gangliosides are able to selectively act where mechanisms responsible for neurotoxicity have been activated, thus antagonizing the effects of the paroxistic and continuous stimulation of the excitatory amino acid receptors (Favaron M. et al: Gangliosides prevent glutamate and kainate neurotoxicity in primary neuronal cultures of neonatal rat cerebellum and cortex. Proc. Natl. Acad. Sci. 85: 7351–7355, 1988)

Concerning the PNS, the effects of the ganglioside mixture have been reported in models of traumatic (Gorio A. et al., Brain Res. 197: 236241, 1980), metabolic (Norido F. et al., Exp. Neurol. 83: 221–232, 1984) and toxic (Di Gregorio F. et al., Cancer Chemother. Pharmacol. 26: 3136, 1990) neuropathies. Concerning the CNS, the positive effects of recovery induced by the monosialoganglioside $GM_1$ have been widely described in ischemia models (Karpiak S. E. et al., CRC Critical Rev. in Neurobiology, vol. 5. Issue 3, pp. 221–237, 1990), as well as in traumatic (Toffano G. et al., Brain Res. 296: 233–239, 1984) and neurotoxic (Schneider et al., Science 256: 843–846, 1992) lesions. Such results have led to the clinical application of $GM_1$ in conditions of ischemic brain injury (Argentino C. et al., Stroke 20: 1143–1149, 1989) and in conditions of traumatic injury of the spinal cord (Geisler F. H., N. Engl. J. Med. 324: 1829–1838, 1991).

In addition, it has been recently shown that gangliosides are involved in the modulation of the expression of the receptors named $CD_4$, which are present on the membrane of some lymphocytes and furthermore it has been shown that such a modulation is associated with an inhibition of the proliferation of the HIV virus (Offner H. et al.: Gangliosides induce selective modulation of $CD_4$ from helper T lymphocytes. J. Immunol. 139: 3295–3305, 1987; Grassi F. et al.: Chemical residues of ganglioside molecules involved in interactions with lymphocyte surface targets leading to $CD_4$ masking and inhibition of mitogenic proliferation. Eur. J. Immunol. 20: 145–150, 1990; Chieco-Bianchi et al. $CD_4$ modulation and inhibition of HIV-1 infectivity induced by monosialoganglioside $GM_1$ in vitro. AIDS 3:501–507, 1989).

The molecule named $CD_4$ is a membrane glycoprotein of 55 KDa expressed by thymocytes, by a "subset" of T lymphocytes and, at a lower density, by monocytes/macrophages. The molecule can be divided into three portions: one extracellular that is divided into 4 domains, three of which have a structure that joins them to the superfamily of immunoglobulins, an intra-membrane portion of 21 amino acids (aa), and a intracytosolic portion of 40 basic aa.

In T lymphocytes $CD_4$ has at least two functions. On one hand, it interacts with a non-polymorphic region of Class II HLA molecules, thus stabilizing the bond between T cell and the cell which expresses the antigen (secondary role). On the other hand, recent evidence have shown how the interaction of $CD_4$ with its own ligand induces the activation of a cytoplasmic tyrosine kinase (named p56 lck) that is in contact with the intracytosolic portion of $CD_4$. The activation of the tyrosine kinase and the subsequent phosphorylation of different substrates, among them the gamma chain of $CD_3$, has a facilitatory role in the signal transduction following the interaction between the antigen receptor and the antigen itself. Hence, $CD_4$ has an active role in the mechanisms that regulate the activation of T lymphocytes.

In addition to these relevant functions for the physiology of T cells, $CD_4$ is also the receptor utilized by HIV viruses to enter the target cells.

The $CD_{4+}$ T lymphocytes play a major role in immune system functioning. In the majority of cases, following contact with the antigen the first cells responsible for any adaptative response are the $CD_{4+}$ T cells, which, after the activation, may become in turn effectors of response. Alternatively, the activated $CD_{4+}$ cells can help, by release of cytokines, other cells (B cells, $CD_{8+}$ T cells) to become effectors of response. This is valid both for responses against foreign antigens (non-self) and for body antigens (self). Thus, $CD_{4+}$ T cells are primarily involved in several autoimmune diseases.

The possibility of modulating the $CD_{4+}$ T cell function is relevant in a wide range of human pathologies.

In different models, both in vitro and in vivo it has been shown that by blocking the $CD_4$ molecule with monoclonal antibodies, the function of $CD_{4+}$ T cells is inhibited. Such an inhibition leads in turn to unsuccessful proliferation, unsuccessful production of cytokines, unsuccessful production of antibodies, and suppression or lowering of clinical expression of autoimmune symptoms in experimental models of autoimmune pathology.

The pharmacological properties of the new O-sulfated derivatives, according to the present invention, can be emphasized by the experimental studies performed on the following compounds:

O-SULFATED $GM_1$ (Liga 135)
O-POLYSULFATED $GM_1$ (Liga 161)
O-SULFATED $GM_2$ (Liga 181)
O-SULFATED $GM_3$ (LIGA 182)

Liga 135, Liga 161, Liga 181 and Liga 182 are prepared as described in Examples 1, 2, 3, and 4, respectively.

Hereinafter will be described the experimental models and the results obtained with some exemplary compounds which are object of the present invention.

1. Antineurotoxic effect of Liga 135 and 161 in vitro in cerebellar granule cells: protective effect against neurotoxicity induced by exogenous glutamate.

MATERIALS AND METHODS

Cell cultures

Primary cultures of cerebellar granule cells have been prepared from 8-day-old Sprague-Dawley rats.

Neurons have been grown in 35 mm dishes for 11–13 days and kept in a humidified environment (95% air and 5% $CO_2$) at 37° C. Cultures ($2.5 \times 10^6$ cells/dish) were mainly constituted of granule cells (>95%) with a low percentage (<5%) of glial cells (Gallo V. et al.: Selective release of glutamate from cerebellar granule cells differentiating in culture. Proc. Natl. Acad. Sci. USA 79, 7919–7923, 1982). Glial proliferation was prevented by cytosine arabinofuranoside.

The Liga 135 and 161 derivatives have been solubilized in sterile water at the concentration of 50 mM and dissolved at different concentrations in Locke's solution (154 mM NaCl, 5.6 mM KCl, 3.6 mM $NaHCO_3$, 2.3 mM $CaCl_2$, 1 mM $MgCl_2$, 5.6 mM glucose, 4.6 mM Hepes, pH 7.4).

Concentrations from 200 $\mu$M to 5 $\mu$M have been tested. Description of the model of neurotoxicity induced by exogenous glutamate: compound in a pretreatment paradigm.

The cell culture medium was aspirated from the dishes (and properly stored). The dishes were washed (3×2 ml) with Locke's solution, then the solutions (1.5 ml) containing the compound to be tested were added, and incubated for 2 hrs in incubator at 37° C. (5% $CO_2$).

The treated cells were washed (3×2 ml) with Locke's solution +10% heat-inactivated fetal calf serum (without glutamic acid), then washed (3×2 ml) in Locke's solution in the absence of $Mg^{2+}$. Glutamate was added at 100 $\mu$M (1.5 ml) in Locke's solution (–$Mg^{2+}$) or Locke's solution alone ($Mg^{2+}$) was used (controls). The incubation with glutamate or with Locke's solution (–$Mg^{2+}$) was performed for 60 minutes at room temperature (27° C.). The glutamate was then removed, the dishes were washed with Locke's solution (+$Mg^{2+}$) (2×2 ml), then incubated in the presence of the initial medium (properly stored) for 24 hrs at 37° C. in incubator (5% $CO_2$).

At the end of the incubation the cell viability measured by using the MTT calorimetric test was evaluated (Mosmann T., Rapid calorimetric assay for cellular growth and survival: application to proliferation and cytotoxicity assays. J. Immunol. Meth. 65, 55–63, 1983 and modified according to Skaper S. D. et al.: Death of cultured hippocampal pyramidal neurons induced by pathological activation of N-methyl-D-aspartate receptors is reduced by monosialogangliosides. J. Pharm. and Exp. Ther. 259, 1, 452–457, 1991). The data are expressed as $ED_{50}$ ($\mu$M).

RESULTS

The obtained results (Table 1) show that both compounds have a marked antineurotoxic activity: the neuroprotective effect (around 100%) of Liga 135 and 161 has been observed at concentrations of 50 and 25 $\mu$M, respectively.

TABLE 1

Antineuronotoxic effect of Liga 135 and 161 in cerebellar granule cells: protective effect on neurotoxicity induced by exogenous glutamate

| Groups | $ED_{50}$ |
| --- | --- |
| 1) glutamate + Liga 135 | 20 $\mu$M |
| 2) glutamate + Liga 161 | 10 $\mu$M |

2. Antineurotoxic effect of Liga 161, 181 and 182 in vitro in cerebellar granule cells: compound in cotreatment paradigm with glutamic acid.

MATERIALS AND METHODS

Cell cultures

Primary cultures of cerebellar granule cells have been prepared according to the method described in Materials and Methods of the preceding experiment (1).

The Liga 161, 181 and 182 derivatives have been dissolved in sterile water at a concentration of 50 mM. Thus, dilutions have been performed at different concentrations in Locke's solution (154 mM NaCl, 5.6 mM KCl, 3.6 mM $NaHO_3$, 2.3 mM $CaCl_2$, 5.6 mM glucose, 4.6 mM Hepes, pH 7.4).

Concentrations from 100 $\mu$M to 5 $\mu$M have been tested.
Description of the model of neurotoxicity induced by exogenous glutamate: compound in cotreatment paradigm with glutamic acid The cell culture medium was aspirated from the dishes (and properly stored). The dishes were washed (3×2 ml) with Locke's solution in the absence of $Mg^{2+}$. Then, 1.5 ml of Locke's solution ($-Mg^{2+}$) with and without 100 $\mu$M glutamate and with and without the compound to be tested were added. The incubation period lasted 30 minutes (37° C.). Glutamate and the compound to be tested were then removed. The dishes were washed with Locke's solution in the presence of $Mg^{2+}$ (2×2 ml) and then incubated in the presence of the initial medium (properly stored) for 24 hours at 37° C. in an incubator (5% $CO_2$).

At the end of the incubation cell viability measured by means of the MTT colorimetric test was evaluated (Mosmann T.: Rapid colorimetric assay for cellular growth and survival: application to proliferation and cytotoxicity assays. J Immunol. Meth. 65, 55–63, 1983 and modified according to Skaper S. D. et al.: Death of cultured hippocampal pyramidal neurons induced by pathological activation of N-methyl-D-aspartate receptors is reduced by monosialogangliosides. J. Pharm. and Exp. Ther. 259,1, 452–457, 1991). Data were expressed as $ED_{50}$ ($\mu$M).

RESULTS

The data obtained (Table 2) show that the new derivatives have a marked antineurotoxic activity, even when administered simultaneously with glutamate (co-treatment): the neuroprotective effect reaches its maximum effect (around 100%) at 100 $\mu$M.

TABLE 2

Antineurotoxic effect of Liga 161, 181 and 182 in simultaneous treatment with exogenous glutamate in cerebellar granule cells (protective effect).

| Groups | $ED_{50}$ |
|---|---|
| 1) glutamate + Liga 161 | 48 $\mu$M |
| 2) glutamate + Liga 181 | 44 $\mu$M |
| 3) glutamate + Liga 182 | 58 $\mu$M |

3. Neuritogenic activity of the compounds Liga 135 and Liga 161

MATERIALS AND METHODS
Cell Cultures

Mouse neuroblastoma cells C1300, Neuro-2A clone (obtained from American Cell Type Culture Collection—Bethesda, Md.) have been seeded at a density of 10,000 cells/well (24-Falcon) in tissue culture medium containing Dulbecco's modified Eagle medium (DMEM, Gibco), 10% heatinactivated fetal calf serum (FCS, lot 7201 Seromed), penicillin (100 units per ml, Irvine) and L-glutamine (2 mM, Sigma) Cells have been incubated at 37° C. for 24 hr, then the medium was withdrawn and substituted with 350 $\mu$l of fresh culture medium with and without compounds to be tested.

Compounds under examination and their solubilization

The derivatives have been solubilized in sterile water.

For the different compounds, consecutive dilutions in tissue culture medium (concentrations from 200 $\mu$M to 5 $\mu$M) were performed.

Parameters

Neuritogenic activity (% of neurite-bearing cells under the optical microscope).

Culture dishes incubated with the tested compounds were analyzed under a phase contrast microscope (250×): 9 optical fields were chosen with prefixed coordinates and photographed. Then, the total number of cells were counted, as well as the number of neurite-bearing cells (length at least double of the cell diameter) in blind on every picture. The percentage of neurite-bearing cells was determined following the counting of at least 100 cells, and the data were expressed by the respective $ED_{50}$ ($\mu$M) (Facci L. et al.: Promotion of neuritogenesis in mouse neuroblastoma cells by exogenous ganglioside $GM_1$. J. Neurochem. 229–305, 1984).

RESULTS

The results obtained (Table 3) show that the Liga 135 and 161 derivatives promote neuritogenesis in vitro. In particular, in the experimental conditions tested, it turns out that:

the neuritogenic effect with Liga 161 is maximal at a dose of 200 $\mu$M (about 58% of the cells present very long and ramified neurites).

the neuritogenic effect with Liga 135 is maximal at a dose of 200 $\mu$M (about 54% of the cells present very long and branched neurites).

TABLE 3

Neuritogenic effect of Liga 135 and 161 in neuroblastoma cells N2A

| Compounds | $ED_{50}$ ($\mu$M) |
|---|---|
| Liga 135 | 55 $\mu$M |
| Liga 161 | 68 $\mu$M |

4. Effect of Liga 182 on the expression of the $CD_4$ molecule in Molt 3 cells

Molt 3 cells (American Type Culture Collection—Rockville, Md., USA) have been utilized, human tumoral cell lines derived from an acute lymphoblastic leukemia and formed by T lymphocytes expressing $CD_4$ on their surface. Such a cell line was chosen due to the fact that it overlaps, as regards the expression of the $CD_4$ molecule, human T lymphocytes obtained from peripheral blood. 100% of Molt 3 cells express $CD_4$, whereas only part of human T lymphocytes from peripheral blood express $CD_4$ in a proportion varying from subject to subject. The Molt 3 model has therefore the advantage of allowing a better experimental reliability.

MATERIALS AND METHODS

Molt 3 cells ($1 \times 10^6$) have been incubated with different concentrations of Liga 182 (from 1 $\mu$g/ml to 500 $\mu$g/ml) for 60 minutes at 37° C. in buffered saline (PBS), with or without Fetal Calf Serum (FCS). When utilized, FCS was added at a concentration of 5 or 10 part/percentage (vol/vol). Following the incubation and the subsequent washing the percentage of cells expressing $CD_4$ has been measured by flow cytof luorimetry using a monoclonal, fluoresceinated (mAb), specific for $CD_4$ (DAKO T4, Dakopatts, Glostrup, Denmark) and a cytofluorimeter (EPICS V, Coulter Electronics, Hialeah, Fla., USA).

In Table 4 are reported the data concerning the percentage of Molt 3 cells that express $CD_4$, following the incubation with the compound under examination at the different concentrations utilized.

TABLE 4

Effect of Liga 182 on the expression of $CD_4$ in Molt 3 cells
% MOLT-3 cells expressing $CD_4$ on the surface

| Compound | µg/ml | FCS (%) 0 | 5 | 10 |
|---|---|---|---|---|
| Liga 182 | 0 | 95.5 | 98.9 | 98.9 |
| Liga 182 | 10 | 0.2 | — | — |
| Liga 182 | 50 | 0.5 | — | — |
| Liga 182 | 100 | 0.9 | 0.1 | 53.7 |
| Liga 182 | 200 | — | 0 | 0.1 |
| Liga 182 | 500 | — | 0 | 0 |

The results reported in Table 4 show how the modulating effect of Liga 182 is a function of a dose/response curve, and how increasing doses of serum require increasing concentrations of Liga 182.

It is important to point out that, at the highest concentration of serum, the Liga 182 compound is able to totally inhibit the expression of $CD_4$.

CONCLUSIONS

The above-described results show a remarkably interesting pharmacological profile of the novel compounds, which are object of the present invention. Special mention should be made of the antineurotoxic effect on CNS cells, and the modulatory effect on the expression of the $CD_4$ molecule in the immune system cells.

In consideration of the antineurotoxic effect, the novel derivatives of the neuraminic acid may be used in disorders associated with an excitatory activity of the excitatory amino acids. It has been demonstrated that such amino acids, e.g., the glutamic or aspartic acid, besides their major role in different physiological processes, e.g. synaptogenesis and neuronal plasticity, are involved in the etiogenesis and/or evolution of different disorders with neuronal dysfunctions and/or death. Even though neuronal damage may have different causes, the neuronal dysfunctions trigger a cascade of cellular events, such as the activation of enzymatic reactions depending on $Ca^{+2}$ ions, the influence of $Ca^{+2}$ ions, the activation of secondary messengers, which result in neuronal death. Damage to the CNS caused by excitatory amino acids appear for instance in ischemia, epilepsy, trauma, compression, metabolic dysfunctions, aging, toxic-infective disorders, as well as in chronic neurodegenerative disorders, such as Alzheimer's disease or Huntington's chorea (Engelsen B., Acta Neurol. Scand. "Neurotransmitter glutamate: its clinical importance", 186, 4, 337–355; Olney J. W., Annu. Rev. Pharmacol. Toxicol., "Excitatotoxic amino acids and neuropsychiatric disorders", 1990, 30, 47–71).

In addition, the novel compounds which are object of the present invention, in consideration of their neurite-promoting activity, may be used with advantage in the therapies aiming at nerve function recovery in those pathologies associated with a neuronal damage, such as peripheral neuropathies.

Moreover, the capacity of such compounds to modulate the expression of the $CD_4$ molecule on immune cell surface, may be of great relevance in a great range of human pathologies, e.g., those situations in which it is necessary to prevent and/or treat infections in which $CD_4$ cells are involved (especially infections the etiological agents thereof are microorganisms belonging to the HIV virus family). Furthermore, $CD_4$ modulation is useful in systemic autoimmune or organ-specific diseases, such as multiple sclerosis, rheumatoid arthritis, chronic polyarthritis, lupus erythematosus, juvenile-onset diabetes mellitus and in order to prevent the phenomenon of organ transplant rejection as well as rejection by the transplanted material against the host, as in the case of bone marrow transplant, and in all cases where the desired effect is to obtain tolerance towards "self" and "non-self" antigens.

The present invention does not include derivatives such as totally persulfated $GM_1$, $GD_{1a}$, $GD_{1b}$, and $GT_{1b}$, whereof the modulatory effect of $CD_4$ and the proliferation inhibition of the HIV-1 virus are already known, whereas the present invention includes the therapeutical use of the aforesaid compounds in consideration of their antineurotoxic and neuritogenic activity, both in direct therapeutical procedures and in the preparation and use of pharmaceutical compositions comprising said compounds.

The present invention includes also a process for the preparation of the novel compounds. Such a process involves conventional and well-documented approaches for the esterification with sulfuric acid of the hydroxyl groups. Thus, the process for the preparation of novel compounds consists in treating a ganglioside, a N-acyl-N,N'-dilyso-ganglioside, a N'-acyl-N,N'-dilyso-ganglioside, or a N,N'- or polyacyl-N,N'-dilyso-ganglioside with sulfuric acid or its reactive derivative and, optionally, in the conversion of sialic carboxylic groups or free hydroxyl groups into their functional derivatives and optionally converting the obtained compounds into their metal salts or salts deriving from organic bases, or into their salts with acids.

The process also involves those modifications in which the process is interrupted during any phase and, if desired, the remaining steps are performed later, or in which the process starts from an intermediate and the remaining steps are performed or in which an "in situ" intermediate is formed.

The lyso-gangliosides may be prepared from gangliosides by alkaline hydrolysis, for example with tetra-alkylammonium hydroxides, sodium hydroxide or others.

The preparation of N- or N'-mono or poly-acyl-derivatives from N,N'-dilyso-gangliosides is described in literature.

Compounds having an acyl group on the neuraminic nitrogen can be prepared by various methods. It is possible, for example, to start with dilyso-gangliosides and then effect an intermediate provisional protection of the sphingosine amino group, which can be done for example by hydrophobic interaction with phosphatidylcholine, or by acylation with suitable protective groups, subsequent acylation on the neuraminic nitrogen with a derivative of the acid which is to be introduced into this position, and then deprotection on the sphingosine nitrogen. Lastly, dilyso-gangliosides can be acylated on the two amino groups with the same acid and the diacyl compound can be exposed to the action of enzymes which are able to selectively remove the acylamino groups from the sphingosine nitrogen, for example enzymes used to obtain lyso-gangliosides from gangliosides, such as the glycosphingolipid-ceramide-deacylase enzyme (see plan 1). N-monoacyl-N,N'-dilyso-gangliosides can however also be obtained by deacylating N,N'-diacyl-N,N'-dilyso-gangliosides on the neuraminic nitrogen by selective chemical hydrolysis, for example with 0.1 molar alcoholic potassium hydroxide.

The procedure for the preparation of N-acyl-N,N'-dilyso-gangliosides, and N'-acyl-N,N'-dilyso-gangliosides and N,N'-diacyl-N,N'-dilyso-gangliosides, comprises acylating N,N'-dilyso-gangliosides with the acids corresponding to the acyl groups to be introduced, optionally followed by selectively deacylating suitable N,N'-diacyl-N,N'-dilyso-gangliosides on the sphingosine or neuraminic nitrogen.

It is also possible to acylate N-acyl-N,N'-dilyso-gangliosides or N'-acyl-N,N'-dilyso-gangliosides with acids corresponding to the acyl group to be introduced, for the preparation of N,N'-diacylated derivatives in which the two acyl groups may be different.

N-acylation according to the aforesaid procedure can be effected in the conventional manner, for example by reacting the starting products with an acylating agent, especially with a functional derivative of the acid, the residue of which is to be introduced. Thus, it is possible to use a halogen or an anhydride as the functional derivative of the acid, and the acylation is carried out preferably in the presence of a tertiary base, such as pyridine or collidine. Anhydrous conditions can be used at room temperature or at higher temperatures, or the Schotten-Baumann method can also be used to advantage, operating in aqueous conditions in the presence of an organic base. In some cases it is also possible to use esters of the acids as reactive functional derivatives. To acylate, it is also possible to use methods with activated carboxy derivatives, such as those used in peptide chemistry, for example the method using mixed anhydrides or derivatives obtainable with carbodiimide derivatives or isoxazole salts. Of all the preparation methods, the following are the most appropriate:

1. reaction of the lyso-ganglioside derivative with the azide of the acid;
2. reaction of the lyso-ganglioside derivative with an acylimidazole of the acid obtainable from the acid with N,N'-carbonyldiimidazole;
3. reaction of the lyso-ganglioside derivative with a mixed anhydride of the acid and of trifluoroacetic acid;
4. reaction of the lyso-ganglioside derivative with the chloride of the acid;
5. reaction of the lyso-ganglioside derivative with the acid in the presence of a carbodiimide (such as dicyclohexylcarbodiimide) and optionally a substance such as 1-hydroxybenzotriazole;
6. reaction of the lyso-ganglioside derivative with the acid by heating;
7. reaction of the lyso-ganglioside derivative with a methyl ester of the acid at a high temperature;
8. reaction of the lyso-ganglioside derivative with a phenol ester of the acid, for example an ester with para-nitrophenol;
9. reaction of the lyso-ganglioside derivative with an ester derived from the exchange between a salt of the acid and 1-methyl-2-chloropyridinium iodide.

It has already been explained how it is possible to obtain selective partial acylation both on the sphingosine and on the neuraminic nitrogen. Scheme 1 illustrates these procedures.

Enzymatic deacylation of N,N'-diacyl-N,N'-dilyso-gangliosides on the sphingosine nitrogen as previously reported can be effected under the same conditions as those used for the partial deacylation of gangliosides, for example as described in J. Biochem., 103, 1 (1988). The double deacylation of N,N'-diacyl-N,N'-dilyso-gangliosides to N,N'-dilyso-gangliosides can be effected in the same way as the preparation of de-N-acetyl-lyso-gangliosides as described for example in Biochemistry 24, 525 (1985); J. Biol. Chem. 255, 7657, (1980); Biol. Chem. Hoppe Seyler 367, 241, (1986): Carbohydr. Research 179, 393 (1988); Bioch. Bioph. Res. Comn. 147, 127 (1987).

The aforesaid publication in Carbohydr. Research 179 also describes a method for selective deacylation on the neuraminic nitrogen by the action of KOH (0.1M) in 90% normal butanol with the ganglioside $GM_3$. This type of deacylation reaction can be applied to N,N'-diacyl-N,N'-dilyso-gangliosides to obtain N-acyl-N,N'-dilyso-gangliosides.

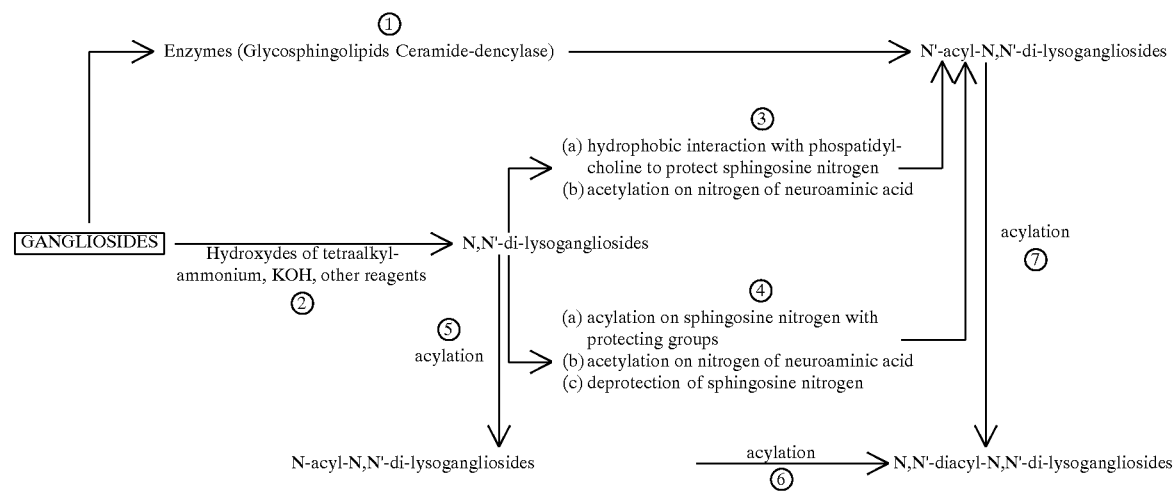

SCHEME 1

The preferred method for the esterification of hydroxyl groups according to the process of the present invention is performed preferably with a reactive derivative of sulfuric acid, preferably by treatment with a sulfur trioxide/dimethylformamide complex in the presence of a base, such as triethylamine, or with sulfur trioxide/trimethylamine in dimethylformamide complex, then with trifluoroacetic acid in dichloromethane (Compare Biochemical and Biophysical Research Communications, Vol. 175, No. 1, Feb. 28th, 1991). With such methods, which can vary according to temperature condition, solvents used and duration of the reaction, it is possible to obtain partial sulfuric esters of the hydroxyl groups or total esters, hence persulfated compounds.

The functional modification to be eventually performed, if desired, on the compounds obtained from the conversion with the said derivatives of sulfuric acid, is also done according to well-known methods, thus excluding those methods which could affect the basic ganglioside structure, such as involving highly acid agents, or which would be anyway performed in critical alkaline or acid conditions, or even those methods which would bring forth to an unwanted alkylation of the hydroxyl groups of the saccharide, sialic or ceramide portion.

The esterification of the sialic carboxyl groups or their conversion into amides can be performed for example as described in the U.S. Pat. No. 4,713,374 of 15 Dec. 1987.

Amides can be prepared for example according to the following methods:

a) reaction of the carboxyl esters with ammonia or amines;

b) reaction of derivatives according to the invention with carboxyl groups activated with ammonia or amines.

Acylation of the hydroxyl groups on the saccharide, sialic and ceramide portion can be performed for example by means of an acid halide or an acid oxide, preferably in the presence of a tertiary base.

Another aspect of the present invention is directed to pharmaceutical preparations including, as active ingredients, one or more of the novel compounds and, in particular, those above emphasized. Such preparations can be formulated for oral, rectal, parenteral, local or transdermal administration, thus being in a solid or semisolid form, for example pills, tablets, gelatine capsules, capsules, suppositories, soft gelatine capsules. For parenteral use predetermined forms for intramuscular or transdermal administration or suitable for infusions or intravenous injection may be used, and they can therefore be prepared as solutions of the active ingredients, or as lyophilized forms of the active ingredients to be mixed with one or more excipients or pharmaceutically acceptable solvents, suitable to these uses and osmolarity-compatible with the physiological fluids.

For local administration preparations in the form of sprays, for example nasal sprays, creams and ointments for topical use or bandages adequately prepared for transdermal administration are considered.

The preparations of the present invention can be administered both to humans and animals. The preparations contain preferably 0.01% to 0.1% of the active ingredient in the case of solutions, sprays, ointments and creams, and 1% to 100%—preferably 5% to 50%—of the active ingredient in the case of solid preparations. Dosage depends on the indication, the desired effect, and preferred route of administration.

The present invention also concerns the therapeutic use of the novel semisynthetic analogues for the above-said indications. The daily dose to be administered in humans by parenteral route (subcutaneous or intramuscular), or by transdermal or oral route, is generally between 0.5 and 5 mg of the active ingredient per kg of body weight. In the preparations reported hereinafter a dose of 150 mg per unit can be reached. The daily dose may be divided in two or more partial doses to be administered at intervals.

The following examples illustrate the preparation of the novel semisynthetic analogues which are object of the present invention, as well as the preparations that contain them as active ingredients.

EXAMPLE 1
O-SULFATED $GM_1$ (Liga 135)

500 mg (0.31 mmoles) of $GM_1$ are dissolved in 5 ml of anhydrous dimethylformamide. 0.44 ml (3.2 mmoles) of triethylamine and 245 mg (1.6 mmoles) of sulfur trioxide/dimethylformamide complex are then added.

React under stirring at room temperature for 5 hours, then precipitate in 10 volumes of acetone. Dissolve the raw compound in 50 ml of 1% $Na_2CO_3$, dialyze against $H_2O$ and then lyophilize.

Yielded product: 480 mg.

Chromatographed on silica-gel plate with chloroform/methanol/$CaCl_2$ 0.3% 60/35/8, the product shows a $R_f$ between 0.3 and 0.4. Molar ratio of sulfate/neuraminic acid groups 1/1 (determination of sulfate groups by ion chromatography and determination of neuraminic acid using the resorcinol method).

Characteristic absorption I.R. S=O groups: 1260 $cm^{-1}$ (KBr).

EXAMPLE 2
O-POLYSULFATED $GM_1$ (Liga 161)

500 mg (0.32 mmoles) of $GM_1$ are dissolved in 5 ml of anhydrous dimethylformamide. 0.88 ml (6.37 mmoles) of triethylamine and 976 mg (6.37 mmoles) of a sulfur trioxide/dimethylformamide complex are then added.

React under stirring at room temperature for 5 hours, then precipitate in 10 volumes of acetone. Dissolve the raw compound in 50 ml of 1% $Na_2CO_3$, dialyze against $H_2O$ and then lyophilize.

Yielded product: 650 mg.

Chromatographed on silica-gel plate with chloroform/methanol/$CaCl_2$ 0.3% 60/35/8, the product shows a $R_f$ between 0.01 and 0.05. Molar ratio of sulfate/neuraminic acid groups 5/1 (determination of sulfate groups by ion chromatography and determination of neuraminic acid using the resorcinol method).

Characteristic absorption I.R. S=O groups: 1260 $cm^{-1}$ (KBr).

EXAMPLE 3
O-SULFATED-$GM_2$ (Liga 181)

100 mg (0.07 mmoles) of $GM_2$ are dissolved in 1 ml of anhydrous dimethylformamide. Then 100 $\mu l$ (0.7 mmoles) of triethylamine and 54 mg (0.35 mmoles) of sulfur trioxide/dimethylformamide complex are added.

React under stirring at room temperature for 5 hours, then precipitate in 10 volumes of acetone. Dissolve the raw product in 10 ml of 1% $Na_2CO_3$, dialyze against $H_2O$ and then lyophilize.

Yielded product: 126 mg.

Chromatographed on silica-gel plate with chloroform/methanol/$CaCl_2$ 0.3% 60/35/8, the product shows a $R_f$ between 0.01 and 0.1. Molar ratio of the sulfate/neuraminic acid groups 4/1 (determination of sulfate groups by ion chromatography and determination of neuraminic acid using the resorcinol method).

Characteristic absorption I.R. groups S=O: 1260 $cm^{-1}$ (KBr).

EXAMPLE 4
O-SULFATED $GM_3$ (Liga 182)

100 mg (0.08 mmoles) of $GM_3$ are dissolved in 1 ml of anhydrous dimethylformamide. Then, 0.11 ml (0.8 mmoles) of triethylamine and 62.4 mg (0.41 mmoles) of sulfur trioxide/dimethylformamide complex are added.

React under stirring at room temperature for 5 hours, then precipitate in 10 volumes of acetone. Dissolve the raw product in 50 ml of 1% $Na_2CO_3$, dialyze against $H_2O$ and then lyophilize.

Yielded product: 116 mg.

Chromatographed. on silica-gel plate with chloroform/methanol/$CaCl_2$ 0.3% 60/35/8, the product shows a $R_f$ between 0.05 and 0.15. Molar ratio of sulfate/neuraminic acid groups 3/1 (determination of sulfate groups by ion chromatography and determination of neuraminic acid using the resorcinol method).

Characteristic absorption I.R. S=O groups: 1260 cm$^{-1}$ (KBr).

EXAMPLE 5
O-SULFATED N-ACETYL-LYSO $GM_1$ 500 mg (0.37 mmoles) of N-acetyl-lyso $GM_1$ are dissolved into 5 ml of anhydrous dimethylformamide. Then, 0.5 ml (3.7 mmoles) of triethylamine and 283 mg (1.85 mmoles) of the sulfur trioxide/dimethylformamide complex are added.

React under stirring at room temperature for 5 hours, then precipitate in 10 volumes of acetone. The raw product is dissolved in 50 ml of 1% $Na_2CO_3$, dialyzed against $H_2O$ and then lyophilized.

Yielded product: 500 mg.

Chromatographed on silica-gel plate with chloroform/methanol/$CaCl_2$ 0.3% 60/35/8, the product shows a $R_f$ between 0.15 and 0.28. Molar ratio of sulfate/neuraminic acid groups 1/1 (determination of sulfate groups by ion chromatography and determination of neuraminic acid using the resorcinol method).

Characteristic absorption I.R. S=O groups: 1260 cm$^{-1}$ (KBr).

EXAMPLE 6
O-SULFATED N-DICHLOROACETYL-LYSO $GM_1$ 500 mg (0.35 mmoles) of N-dichloroacetyl-lyso $GM_1$ are dissolved into 5 ml of anhydrous dimethylformamide. Then, 0.48 ml (3.5 mmoles) of triethylamine and 268 mg (1.75 mmoles) of the sulfur trioxide/dimethylformamide complex are added.

React under stirring at room temperature for 5 hours, then precipitate in 10 volumes of acetone. The rough product is dissolved in 50 ml 1% $Na_2CO_3$, dialyzed against $H_2O$ and then lyophilized.

Yielded product: 480 mg.

Chromatographed on silica-gel plate with chloroform/methanol/$CaCl_2$ 0.3% 60/35/8, the product shows a $R_f$ between 0.15 and 0.31. Molar ratio of sulfate/neuraminic acid groups 1/1 (determination of sulfate groups by ion chromatography and determination of neuraminic acid using the resorcinol method).

Characteristic absorption I.R. S=O groups: 1260 cm$^{-1}$ (KBr).

EXAMPLE 7
O-SULFATED N-PHENYLACETYL-LYSO $GM_1$ 500 mg (0.35 mmoles) of N-phenylacetyl-lyso $GM_1$ are dissolved into 5 ml of anhydrous dimethylformamide. Then 0.48 ml (3.5 mmoles) of triethylamine and 268 mg (1.75 mmoles) of the sulfur trioxide/dimethylformamide complex are added.

React under stirring at room temperature for 5 hours then precipitate in 10 volumes of acetone. The raw product is dissolved in 50 ml of 1% $Na_2CO_3$, dialyzed against $H_2O$ and then lyophilized.

Yielded product: 470 mg.

Chromatographed on silica-gel plate with chloroform/methanol/$CaCl_2$ 0.3% 60/35/8, the product shows a $R_f$ between 0.15 and 0.30. Molar ratio of sulfate/neuraminic acid groups 1/1 (determination of sulfate groups by ion chromatography and determination of neuraminic acid using the resorcinol method).

Characteristic absorption I.R. S=O groups: 1260 cm$^{-1}$ (KBr).

EXAMPLE 8
O-SULFATED N,N'-DI(DICHLOROACETYL)-DILYSO $GM_1$ 500 mg (0.34 mmoles) of N,N'-di(dichloroacetyl)-N,N'-dilyso $GM_1$ are dissolved into 5 ml of anhydrous dimethylformamide. Then 0.46 ml (3.4 mmoles) of triethylamine and 260 mg (1.7 mmoles) of the sulfur trioxide/dimethylformamide complex are added.

React under stirring at room temperature for 5 hours, then precipitate in 10 volumes of acetone. The raw product is dissolved in 50 ml of 1% $Na_2CO_3$, dialyzed against $H_2O$ and then lyophilized.

Yielded product: 465 mg.

Chromatographed on silica-gel plate with chloroform/methanol/$CaCl_2$ 0.3% 60/35/8, the product shows a $R_f$ between 0.12 and 0.25. Molar ratio of sulfate/neuraminic acid groups 1/1 (determination of sulfate groups by ion chromatography and determination of neuraminic acid using the resorcinol method).

Characteristic absorption I.R. S=O groups: 1260 cm$^{-1}$ (KBr).

EXAMPLE 9
O-SULFATED N'-TRIMETHOXYBENZOYL-N'-LYSO $GM_1$ 500 mg (0.29 mmoles) of N'-trimethoxybenzoyl-N'-lyso $GM_1$ are dissolved into 5 ml of anhydrous dimethylformamide. Then 0.39 ml (2.9 mmoles) of triethylamine and 222 mg (1.45 mmoles) of the sulfur trioxide/dimethylformamide complex are added.

React under stirring at room temperature for 5 hours then precipitate in 10 volumes of acetone. The rough product is dissolved in 50 ml of 1% $Na_2CO_3$, dialyzed against $H_2O$ and then lyophilized.

Yielded product: 455 mg.

Chromatographed on silica-gel plate with chloroform/methanol/$CaCl_2$ 0.3% 60/35/8, the product shows a $R_f$ between 0.20 and 0.35. Molar ratio of sulfate/neuraminic acid groups 1/1 (determination of sulfate groups by ion chromatography and determination of neuraminic acid using the resorcinol method).

Characteristic absorption I.R. S=O groups: 1260 cm$^{-1}$ (KBr).

EXAMPLE 10
INJECTABLE PHARMACEUTICAL PREPARATIONS

| Preparation No. 1 One 2-ml vial contains: | |
|---|---|
| Active ingredient | 5 mg |
| Sodium chloride | 16 mg |
| Citrate buffer pH = 6 | |
| In water for injection, q.s. to | 2 ml |
| Preparation No. 2 One 2-ml vial contains: | |
| Active ingredient | 50 mg |
| Sodium chloride | 16 mg |
| Citrate buffer pH = 6 | |
| In water for injection, q.s. to | 2 ml |
| Preparation No. 3 One 4-ml vial contains: | |
| Active ingredient | 100 mg |
| Sodium chloride | 32 mg |
| Citrate buffer pH = 6 | |
| In water for injection, q.s. to | 4 ml |

EXAMPLE 11
PHARMACEUTICAL PREPARATIONS IN TWO VIALS

These preparations are prepared in two vials. The first vial contains the active ingredient in the form of a lyophilized powder in quantities varying from 10% to 90% in weight, together with a pharmaceutically acceptable excipient, such a glycine or mannitol. The second vial contains a solvent, such as sodium chloride and a citrate buffer.

The contents of both vials are mixed up immediately before administration and the lyophilized active ingredient is rapidly dissolved, thus resulting in an injectable solution.

Method No. 1 a. One 2-ml vial of lyophilized powder contains:

| | |
|---|---|
| Active ingredient | 5 mg |
| Glycine | 30 mg | b. One 2-ml vial of solvent contains:

| | |
|---|---|
| Sodium chloride | 16 mg |
| Citrate buffer | |
| In water for injection, q.s. to | 2 ml |

Method No. 2 a. One 3-ml vial of lyophilized powder contains:

| | |
|---|---|
| Active ingredient | 5 mg |
| Mannitol | 40 mg | b. One 2-ml vial of solvent contains:

| | |
|---|---|
| Sodium chloride | 16 mg |
| Citrate buffer | |
| In water for injection, q.s. to | 2 ml |

Method No. 3 a. One 3-ml vial of lyophilized powder contains:

| | |
|---|---|
| Active ingredient | 50 mg |
| Glycine | 25 mg | b. One 3-ml vial of solvent contains:

| | |
|---|---|
| Sodium chloride | 24 mg |
| Citrate buffer | |
| In water for injection, q.s. to | 3 ml |

Method No. 4 a. One 3-ml vial of lyophilized powder contains:

| | |
|---|---|
| Active ingredient | 50 mg |
| Mannitol | 20 mg | b. One 3-ml vial of solvent contains:

| | |
|---|---|
| Sodium chloride | 24 mg |
| Citrate buffer | |
| In water for injection, q.s. to | 3 ml |

Method No. 5 a. One 5-ml vial of lyophilized powder contains:

| | |
|---|---|
| Active ingredient | 150 mg |
| Glycine | 50 mg | b. One 4-ml vial of solvent contains:

| | |
|---|---|
| Sodium chloride | 32 mg |
| Citrate buffer | |
| In water for injection, q.s. to | 4 ml |

Method No. 6 a. One 5-ml vial of lyophilized powder contains:

| | |
|---|---|
| Active ingredient | 100 mg |
| Mannitol | 40 mg | b. One 4-ml vial of solvent contains:

| | |
|---|---|
| Sodium chloride | 32 mg |
| Citrate buffer | |
| In water for injection, q.s. to | 4 ml |

Method No. 7 a. One 3-ml vial contains:

| | |
|---|---|
| Active ingredient | |
| Micronized sterile | 40 mg | b. One 3-ml vial of solvent contains:

| | |
|---|---|
| Tween 80 ® | 10 mg |
| Sodium chloride | 24 mg |
| Phosphate buffer | |
| In water for injection, q.s. to | 3 ml |

Method No. 8 a. One 5-ml vial contains:

| | |
|---|---|
| Active ingredient | |
| Micronized sterile | 100 mg | b. One 4-ml vial of solvent contains:

| | |
|---|---|
| Tween 80 ® | 15 mg |
| Soybean lecithin | 5 mg |
| Sodium chloride | 36 mg |
| Citrate buffer | |
| In water for injection, q.s. to | 4 ml |

EXAMPLE 12
PHARMACEUTICAL PREPARATIONS FOR TRANSDERMAL ADMINISTRATION

Preparation No. 1
A bandage contains:

| | |
|---|---|
| Active ingredient | 100 mg |
| Glycerol | 1.6 g |
| Polyvinyl alcohol | 200 mg |
| Polyvinyl pyrrolidone | 100 mg |
| Excipient to increase transdermal penetration | 20 mg |
| Water | 1.5 g |

Preparation No. 2
100 g ointment contain:

| | |
|---|---|
| Active ingredient | 4.0 g |
| (In 5 g phospholipid liposomes) | 4.0 g |
| Polyethylene glycol monostearate | 1.5 g |
| Glycerol | 1.5 g |
| Beta-oxybenzoic acid ester | 125 mg |
| Water | 72.9 g |

EXAMPLE 13
PHARMACEUTICAL PREPARATIONS FOR ORAL ADMINISTRATION

Preparation No. 1
A tablet contains:

| | |
|---|---|
| Active ingredient | 20 mg |
| Single-crystal cellulose | 150 mg |
| Lactose | 20 mg |
| Starch | 10 mg |
| Magnesium stearate | 5 mg |

Preparation No. 2
A pill contains:

| | |
|---|---|
| Active ingredient | 30 mg |
| Carboxymethyl cellulose | 150 mg |
| Starch | 15 mg |
| Lactose | 10 mg |
| Sucrose | 35 mg |
| Coloring agent | 0.5 mg |

Preparation No. 3
A gelatine capsule contains:

| | |
|---|---|
| Active ingredient | 40 mg |
| Lactose | 100 mg |
| Gastroresistant covering | 5 mg |
| Preparation No. 4 | |
| A soft gelatine capsule contains: | |
| Active ingredient | 50 mg |
| Vegetable oil | 200 mg |
| Beeswax | 20 mg |
| Gelatine | 150 mg |
| Glycerol | 50 mg |
| Coloring agent | 3 mg |

This invention being thus described, it is obvious that these methods can be modified in various ways. Such modifications are not to be considered as divergences from the very spirit and purposes of the invention, and any modification that would appear evident to an expert in the field comes within the scope of the following claims:

We claim:

1. Sulfated ester derivatives of gangliosides, N-acyl-N-lyso-gangliosides, N'-acyl-N'-lyso-gangliosides, N-acyl-N,N'-dilyso-gangliosides, N'-acyl-N,N'-dilyso-gangliosides, N,N'-di-lyso-gangliosides and poly-acyl-N,N'-di-lyso-gangliosides having saccharide, sialic and ceramide residues with hydroxyl groups, wherein at least one of the hydroxyl groups is esterified with sulfuric acid to form sulfate groups so that the molar ratio of sulfate groups to sialic residues is from 1:1 to 5:1; and inorganic base, organic base and acid addition salts thereof; and esters and amides of the sialic carboxyl groups; and inner esters between the sialic carboxyl groups and saccharide hydroxyl groups.

2. A mixture of sulfated ester derivatives according to claim 1, wherein said derivatives comprise two or more different mono-sulfated positional isomers and sodium salts thereof.

3. The sulfated ester derivatives according to claim 1 having a plurality of sulfated hydroxyl groups.

4. The sulfated ester derivatives according to claim 1, which are N-acyl-N,N'-dilyso-gangliosides or N'-acyl-N,N'-dilyso-gangliosides having an acyl residue of an aliphatic acid with a maximum of 24 carbon atoms.

5. The sulfated ester derivatives according to claim 4, wherein the acyl residue is substituted with a polar group selected from the group consisting of halides, free or esterified hydroxyl groups, and free or esterified mercapto groups.

6. The sulfated ester derivatives according to claim 1, which are N-acyl-N,N'-dilyso-gangliosides or N'-acyl-N,N'-dilyso-gangliosides having an acyl residue of benzoic acid, wherein said benzoic acid residue has a phenyl group which may be substituted with (1) 1 to 3 $C_{1-4}$ alkyl or alkoxy groups, (2) a free amino group or $C_{1-4}$ alkylamino group, or a combination of groups from (1) and (2).

7. The derivative according to claim 1, in which the acyl group in the N-acyl-N,N'-dilyso ganglioside or N'-acyl-N,N'-dilyso-ganglioside is an acyl moiety of an araliphatic acid with a $C_{24}$ alkylene-aliphatic chain, and wherein a phenyl group may be substituted with 1 to 3 $C_{1-4}$ alkyl or alkoxy groups and/or with a free amino group or $C_{1-4}$ alkylamino groups.

8. The sulfated ester derivatives according to claim 4, wherein the aliphatic acid is cyclopropane, cyclobutane, cyclopentane or cyclohexane carboxylic acid.

9. The sulfated ester derivatives according to claim 1, which are N-acyl-N,N'-dilyso-gangliosides or N'-acyl-N,N'-dilyso-gangliosides having an acyl residue of a heterocyclic acid with one heterocyclic ring and with one heteroatom link selected from the group consisting of —O—, —N=, —NH—, and —S—.

10. The sulfated ester derivatives according to claim 1, which are a carboxylic acid ester of the sialic carboxyl group, said carboxylic acid ester being derived from an aliphatic alcohol having a maximum of 12 carbon atoms or from an araliphatic alcohol having a benzene ring unsubstituted or substituted with 1 to 3 $C_{1-4}$ alkyl groups.

11. The sulfated ester derivatives according to claim 1 which are a carboxylic amide of the sialic carboxyl group, said carboxylic amide being derived from ammonia or from an aliphatic amine with a maximum of 12 carbon atoms.

12. Compounds of claim 1 having the formula

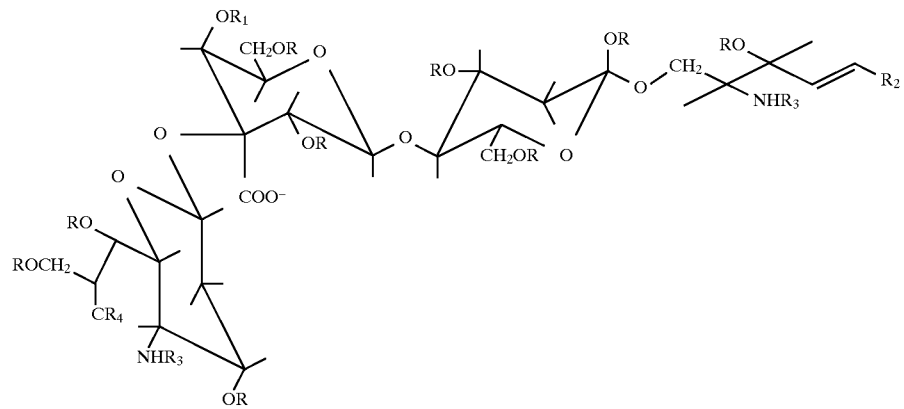

wherein R is hydrogen or $SO_3H$ and $R_1$ is hydrogen, or

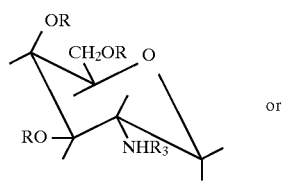 or

-continued

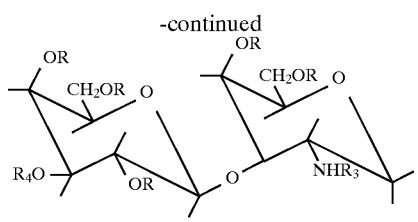

wherein $R_2$ is —$(CH_2)_n$—$CH_3$, n is 12–14,
$R_3$ is hydrogen or acyl, and $R_4$ is hydrogen, or

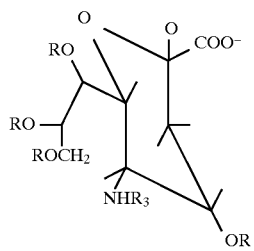

with the proviso that not all R groups can be hydrogen.

13. Sodium salts of the compounds according to claim 12.

14. A compound having a sulfated hydroxyl group selected from the group consisting of mono-sulfated derivatives of:

N-acetyl-lyso-$GM_1$,
N-dichloroacetyl-lyso-$GM_1$,
N-phenylacetyl-lyso-$GM_1$,
N-propionyl-lyso-$GM_1$,
N-trimethylacetyl-lyso-$GM_1$,
N-trimethoxybenzoyl-lyso-$GM_1$,
N-nicotinoyl-lyso-$GM_1$,
N-capronyl-lyso-$GM_1$,
N-octanoyl-lyso-$GM_1$,
N-decanoyl-lyso-$GM_1$,
N-undecanoyl-lyso-$GM_1$,
N-4-chlorobenzoyl-lyso-$GM_1$,
N-4-benzoyl-lyso-$GM_1$, and
N-2-bromoacetyl-lyso-$GM_1$.

15. A compound having one or more sulfated hydroxyl groups selected from the group consisting of mono- and poly-sulfated derivatives of:

N'-acetyl-N'-lyso-$GM_1$,
N'-dichloroacetyl-N'-lyso-$GM_1$,
N'-phenylacetyl-N'-lyso-$GM_1$,
N'-propionyl-N'-lyso-$GM_1$,
N'-trimethylacetyl-N'-lyso-$GM_1$,
N'-trimethoxybenzoyl-N'-lyso-$GM_1$,
N'-nicotinoyl-N'-lyso-$GM_1$,
N'-capronyl-N'-lyso-$GM_1$,
N'-octanoyl-N'-lyso-$GM_1$,
N'-decanoyl-N'-lyso-$GM_1$,
N'undecanoyl-N'-lyso-$GM_1$,
N'-4-chlorobenizoyl-N'-lyso-$GM_1$,
N'-4-benzoyl-lyso-$GM_1$, and
N'-2-bromoacetyl-lyso-$GM_1$, wherein the molar ratio of sulfate groups to sialic residues is from 1:1 to 5:1.

16. A compound having one or more sulfated hydroxyl groups selected from the group consisting of mono- and polysulfated derivatives of N,N'-diacetyl-N,N'-dilyso-$GM_1$,
N,N'-di(dichloroacetyl)-N,N'-dilyso-$GM_1$,
N,N'-di(phenylacetyl)-N,N'-dilyso-$GM_1$,
N,N'-di(propionyl)-N,N'-dilyso-$GM_1$,
N,N'-di(trimethylacetyl)-N,N'-dilyso-$GM_1$,
N,N'-di(trimethoxybenzoyl)-N,N'-dilyso-$GM_1$,
N,N'-di(nicotinoyl)-N,N'-dilyso-$GM_1$,
N,N'-di(capronyl)-N,N'-dilyso-$GM_1$,
N,N'-di(octanoyl)-N,N'-dilyso-$GM_1$,
N,N'-di(decanoyl) -N,N'-dilyso-$GM_1$,
N,N'-di(undecanoyl)-N,N'-dilyso-$GM_1$,
N,N'-di(4-chlorobenzoyl)-N,N'-dilyso-$GM_1$,
N,N'-di(4-benzoyl)-N,N'-dilyso-$GM_1$, and
N,N'-di(2-bromoacetyl)-N,N'-dilyso-$GM_1$, wherein the molar rtio of sulfate groups to sialic residues is from 1:1 to 5:1.

17. Compounds having one or more sulfated hydroxyl groups selected from the group consisting of mono-sulfated and polysulfated derivatives of a ganglioside selected from the group consisting of the following gangliosides: $GM_1$, $GD_{1a}$, $GT_{1b}$, $GM_2$, $GM_3$, $GM_4$, $GM_1$—GlcNAC, $GD_2$, $GD_{1a}$—GalNAC, $GT_{1c}$, $G_Q$, and $GT_1$, wherein the molar ratio of sulfate groups to sialic residues is from 1:1 to 5:1.

18. A method for inhibitingglutamate induced and N-methyl-D-aspartate induced neurocytotoxicity which comprises administering at least one derivative according to claim 1 to a patient in need thereof.

19. A method for inhibiting glutamate induced and N-methyl-D-aspartate induced neurocytotoxicity which comprises administering to a patient in need thereof sulfated $GM_1$, $GD_{1a}$, $GD_{1b}$ and $GT_{1b}$ gangliosides having the hydroxyl sialic acid and ceramide groups thereof esterified with sulfuric acid, wherein the molar ratio of sulfate groups to sialic residues is from 1:1to 5:1.

20. A process for the preparation of a compound according to claim 1, which comprises reacting a ganglioside, a N-acyl-N-lyso-ganglioside N-acyl-N,N'-dilyso-gangliosides, N'-acyl-N,N'-dilyso-gangliosides, a N'-acyl-N'-lyso-ganglioside or a N,N'-di- or poly-acyl-N,N'-dilyso-ganglioside with sulfuric acid to form a partial sulfate ester ganglioside; and optionally converting sialic carboxyl groups or free hydroxyl groups of said partial sulfate ester ganglioside into esters thereof, amides thereof or inner esters between the sialic carboxyl groups and saccharide hydroxyl groups; and optionally converting the partial sulfate ester ganglioside into metal salts or salts deriving from organic bases, or acid addition salts.

21. Pharmaceutical preparations containing, as the active ingredient, a compound according to claim 1, in association with a pharmaceutically acceptable excipient.

22. Pharmaceutical preparations containing as the active ingredients a compound selected from the group consisting of O-SULFATED $GM_1$
O-POLYSULFATED $GM_1$
O-SULFATED $GM_2$ and
O-SULFATED $GM_3$ in association with a pharmaceutically acceptable excipient, wherein the molar ratio of sulfate groups to sialic residues is from 1:1 to 5:1.

23. A method for inhibiting cellular expression of the $CD_4$ molecule in a patient which comprises the administration of at least one of the derivatives of claim 1 to a patient in need thereof.

24. The sulfated ester derivatives according to claim 1, which are N-acyl-N-lyso-gangliosides, N'-acyl-N'-lyso-gangliosides, N-acyl-N,N'-dilyso-gangliosides, N'-acyl-N,N'-dilyso-gangliosides, N,N'-di-lyso-gangliosides.

25. A method for inhibiting glutamate induced and N-methyl-D-aspartate induced neurocytotoxicity which comprises administering at least one compound according to claim 14 to a patient in need thereof.

26. A method for inhibiting glutamate induced and N-methyl-D-aspartate induced neurocytotoxicity which comprises administering at least one compound according to claim 15 to a patient in need thereof.

27. A method for inhibiting glutamate induced and N-methyl-D-aspartate induced neurocytotoxicity which comprises administering at least one compound according to claim 16 to a patient in need thereof.

28. A method for inhibiting cellular expression of the $CD_4$ molecule in a patient which comprises the administration of at least one of the compounds of claim 14 to a patient in need thereof.

29. A method for inhibiting cellular expression of the $CD_4$ molecule in a patient which comprises the administration of at least one of the compounds of claim 15 to a patient in need thereof.

30. A method for inhibiting cellular expression of the $CD_4$ molecule in a patient which comprises the administration of at least one of the compounds of claim 16 to a patient in need thereof.

* * * * *